US00PP21244P2

(12) United States Plant Patent
Kapiteijn

(10) Patent No.: US PP21,244 P2
(45) Date of Patent: Aug. 24, 2010

(54) ***ZANTEDESCHIA* PLANT NAMED 'CAPTAIN AGUILA'**

(50) Latin Name: *Zantedeschia sprengeri*
Varietal Denomination: CAPTAIN AGUILA

(76) Inventor: Anthonius Simon Johannes Kapiteijn, Grasweg 38, Anna Paulowna, LJ (NL) 1761

( * ) Notice: Subject to any disclaimer, the term of this patent is extended or adjusted under 35 U.S.C. 154(b) by 0 days.

(21) Appl. No.: 12/380,510

(22) Filed: Feb. 27, 2009

(51) Int. Cl.
*A01H 5/00* (2006.01)

(52) U.S. Cl. ..... Plt./490

(58) Field of Classification Search ..... Plt./263, Plt./490
See application file for complete search history.

*Primary Examiner*—Susan B McCormick Ewoldt

(57) ABSTRACT

A new and distinct *Zantedeschia* cultivar named 'CAPTAIN AGUILA' is disclosed, characterized by large yellow flowers, prolific flower production, green foliage spotted with white and a short plant height. The new variety is commercially suitable for indoor plant production.

1 Drawing Sheet

Figure 1:
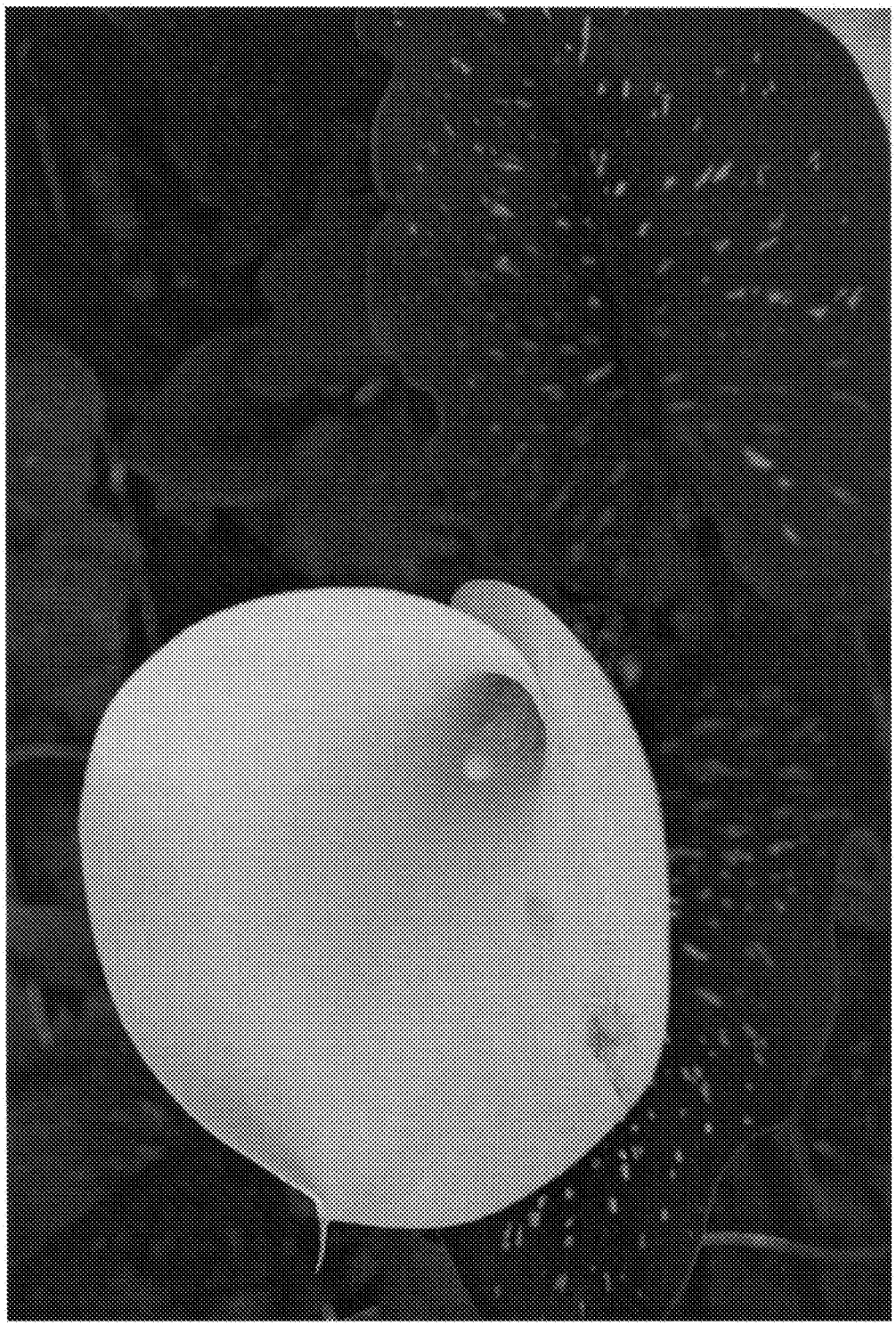

Latin name of the genus and species: *Zantedeschia Sprengeri.*

Variety denomination: 'CAPTAIN AGUILA'.

BACKGROUND OF THE INVENTION

The new cultivar is a product of a planned breeding program. The new variety originated from a cross pollination, made by the inventor in 2002, of a proprietary seed parent identified as '4131' and a proprietary pollen parent identified as '6484', both *Zantedeschia sprengeri.*

The new variety was discovered and selected by the inventor, Anthonius Simon Johannes Kapiteijn, a citizen of the Netherlands, in 2004 in a group of seedlings resulting from the crossing. The new cultivar was found in a commercial green house belonging to the inventor in Anna Paulowna, the Netherlands.

Asexual reproduction of the new cultivar 'CAPTAIN AGUILA' was first performed by micropropagation at a commercial laboratory in Ann Paulowna, the Netherlands in 2005. Micropropagated plants were subsequently grown out to produce tubers. 'CAPTAIN AGUILA' has been reproduced by both micropropagation and tubers and has shown that the unique features of this cultivar are stable and reproduced true to type.

SUMMARY OF THE INVENTION

The cultivar 'CAPTAIN AGUILA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAPTAIN AGUILA.' These characteristics in combination distinguish 'CAPTAIN AGUILA' as a new and distinct *Zantedeschia* cultivar:

1. Large flowers.
2. Prolific flower production.
3. Short plant height.
4. Green foliage with white spots.

PARENT COMPARISON

Plants of the new cultivar 'CAPTAIN AGUILA' are similar to plants of the seed parent variety, '4131' in most horticultural characteristics, however, plants of the new cultivar produce more flowers per plant.

Plants of the new cultivar 'CAPTAIN AGUILA' are similar to plants of the pollen parent variety, '6484' in most horticultural characteristics, however, plants of the new cultivar produce larger flowers.

COMMERCIAL COMPARISON

Plants of the new cultivar 'CAPTAIN AGUILA' are similar to plants of the unpatented variety, *Zantedeschia sprengeri* 'Serrada' in most horticultural characteristics, however, plants of the new cultivar have a different leaf shape and larger flowers.

BRIEF DESCRIPTION OF THE PHOTOGRAPH

The accompanying photograph in FIG. 1 illustrates in full color typical plants of 'CAPTAIN AGUILA' grown in a greenhouse in Anna Paulowna, the Netherlands. The plants are approximately 2 years old, shown growing in ground beds. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'CAPTAIN AGUILA' plants grown in a climate controlled greenhouse in Anna Paulowna, the Netherlands. Night temperature was around 17° C. and day temperature around 24° C. No artificial light, photoperiodic treatments or chemical treatments were given to the plants. Measurements and numerical values represent averages of typical plant types.

Botanical classification: *Zantedeschia sprengeri* cultivar 'CAPTAIN AGUILA.'

PROPAGATION

Time to initiate roots: Approximately 21 days from tissue culture plantlet at approximately 12 to 25° C.
Typical propagation material: Plants for commercial flowering potted plant production are typically produced by planting a 2 year old tuber.
Root description: Fine, fibrous.

PLANT

Growth habit: Leaves growing directly from base of plant, with no stems.
Plant shape: Upright, leaves slightly arching out, as inverted triangle.
Height: Approximately 59.8 cm from soil to top of highest leaf, approximately 86 cm to top of highest spathe.
Plant spread: Approximately 69.6 cm in a 6 inch pot.
Normal pot size: 6 inch and larger.
Growth rate: Moderate.
Branching characteristics: No branching, clump forming. Leaves emerge directly from base of plant.
Number of clumps per plant: 3.
Number of leaves per clump: Average 5.
Number of leaves per plant: Approximately 15.
Age of plant described: Approximately 2 years from tissue culture initiation.

FOLIAGE

Leaf:
*Arrangement.*—Single leaves emerging basally.
*Average length (excluding petiole).*—Approximately 20.8 cm.
*Average width.*—Approximately 16.5 cm.
*Shape of blade.*—Cordate.
*Aspect.*—Entire, undulate; lower half of each leaf more undulate than upper half.
*Apex.*—Aristate.
*Base.*—Hastate.
*Margin.*—Entire.
*Texture of top surface.*—Glabrous, slightly leathery.
*Texture of bottom surface.*—Glabrous, slightly leathery.
*Color.*—Young foliage upper side: Near RHS Green 137B moderately spotted with a few small dots, colored white N155D. Young foliage under side: Near RHS Green 137B moderately spotted with a few small dots, colored white N155D. Mature foliage upper side: Near RHS Green to yellow-green; in between 137A and 147A, moderately dotted white N155D. Average length of dots: 7 mm, average width of dots 1.5 mm. Mature foliage under side: Near RHS Green to yellow-green; in between 137C and 146A, moderately dotted white N155D. Average length of dots: 7 mm, average width of dots 1.5 mm.
Venation:
*Type.*—Pinnate.
*Venation coloration upper side.*—Near RHS Green 141A.
*Venation coloration under side.*—Near RHS Green 143A.
Petiole:
*Length.*—Approximately 55.3 cm.
*Petiole diameter, distal.*—0.7 cm.
*Petiole diameter, proximal.*—1.4 cm.
*Color.*—Near RHS Green; 143B, base greyed-orange 166A and brown 200C.
*Strength.*—Very strong.
*General characteristics.*—Rounded with one shallow rib lengthways, smooth, slightly glossy.
Geniculum: Not present.
Wing:
*Length.*—Approximately 10.8 cm.
*Diameter.*—Approximately 0.5 cm.
*Color.*—Near RHS Yellow-green 145D heavily dotted and striped 200D.

INFLORESCENCE

*Arrangement.*—Spathes with spadices held above the foliage on erect peduncles arising from the leaf axils of the clumps.
*Flowering habit.*—Continuous.
*Quantity of spathes per plant.*—On average 5 fully open spathes in good condition.
*Natural flowering season.*—Autumn to early Spring.
*Time to flowering.*—8 months after planting a 2 year old tuber.
*Fragrance.*—Not present.
*Self-cleaning or persistent.*—Persistent.
*Flower longevity.*—Flowers stay in good condition approximately 60 days on the plant.
Spathe:
*Aspect.*—Strongly cupped, wavy margin.
*Length.*—Approximately 11.2 cm.
*Width.*—Approximately 7.9 cm.
*Depth.*—Approximately 9.8 cm.
*Shape.*—Broad ovate.
*Margin.*—Entire, wavy.
*Apex.*—Mucronate.
*Base.*—Cuneate.
*Color.*—Front when opening: Near RHS Yellow 6A, lighter towards the base, Yellow 5C, with a basal spot (average height: 1.5 cm) greyed-purple 187A.
*Back when opening.*—Near RHS Yellow 6B, lighter towards the base Yellow 5C with a green base 137D and main vein 138A.
*Front when mature.*—Near RHS Yellow 9A, lighter towards the base Yellow 7B, with a basal spot (average height: 1.8 cm) greyed-purple 187A.
*Back when mature.*—Near RHS Yellow 12B, lighter towards the base Yellow 8A with a green base and main vein 137D.
*Fading to.*—Not fading.
Spadix:
*Shape.*—Columnar, slightly tapering towards tip, arising from the top of the peduncle.
*Tip.*—Obtuse.
*Base.*—Obtuse.
*Length.*—Approximately 4.5 cm.
*Diameter.*—Approximately 0.9 cm.
*Color.*—Immature: Lower part (female flowers) Near RHS yellow-green 150C. Upper part (male flowers) Near RHS yellow 13A. Mature: Lower part (female parts) Near RHS yellow-green 150B. Upper part (male parts) Near RHS yellow-orange 17B.
*Quantity of flowers per spadix.*—Approximately 45 female, 300 male.

*Spadix flower arrangement.*—Flowers unisexual, female parts rounded in cross-section, single; male parts irregularly oblong.

*Spadix flower diameter.*—Female parts average: 3.0 mm. Male parts average: 1 mm.

*Spadix flower depth.*—Female parts average: 2 mm. Male parts average: less than 0.5 mm.

Peduncle:

*Length.*—Approximately 69.8 cm.

*Diameter.*—Approximately 0.9 cm.

*Color.*—Near RHS Yellow-green 144A, lighter towards the base, near 150D, marbled with 152B and 152C.

*Strength.*—Moderate.

*Angle.*—Average angle: 10° (straight upright=0°).

REPRODUCTIVE ORGANS

*Anther color.*—Near RHS Yellow-orange 17B.

*Pollen color.*—Near RHS Yellow 4D.

*Quantity pollen.*—Moderate to profuse.

*Stigma color.*—Near RHS Yellow 13A.

*Ovary color.*—Near RHS Yellow-green 150B.

OTHER CHARACTERISTICS

Disease resistance: Neither resistance nor susceptibility to diseases or pests has been observed in this variety.

Drought tolerance and temperature tolerance: The new cultivar is a typical *Zantedeschia,* tolerant of temperatures approximately 9° to 30° C. and does not tolerate drought.

Fruit/seed production: Not observed.

What is claimed is:

1. A new and distinct cultivar of *Zantedeschia* plant named 'CAPTAIN AGUILA' as herein illustrated and described.

* * * * *